(12) United States Patent
Jeong et al.

(10) Patent No.: US 12,287,322 B2
(45) Date of Patent: Apr. 29, 2025

(54) COMPOSITION FOR DETECTING HYDROGEN SULFIDE OR MEASURING HYDROGEN SULFIDE CONCENTRATION AND COMPOSITION COMPRISING SAME AS EFFECTIVE INGREDIENT FOR DIAGNOSING OR IMAGING IN VIVO INFLAMMATION, TISSUES HAVING HYPOXIC DAMAGE, OR CANCER

(71) Applicant: SEOUL NATIONAL UNIVERSITY R&DB FOUNDATION, Seoul (KR)

(72) Inventors: Jae Min Jeong, Seoul (KR); Young Ju Kim, Seoul (KR); Yun-Sang Lee, Seoul (KR); Ji Yong Park, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 1065 days.

(21) Appl. No.: 17/272,636

(22) PCT Filed: Sep. 11, 2019

(86) PCT No.: PCT/KR2019/011848
§ 371 (c)(1),
(2) Date: Mar. 1, 2021

(87) PCT Pub. No.: WO2020/055175
PCT Pub. Date: Mar. 19, 2020

(65) Prior Publication Data
US 2021/0190759 A1    Jun. 24, 2021

(30) Foreign Application Priority Data
Sep. 11, 2018  (KR) .................. 10-2018-0108234

(51) Int. Cl.
  *G01N 33/49* (2006.01)
  *A61K 51/02* (2006.01)
  *A61K 51/04* (2006.01)

(52) U.S. Cl.
  CPC ....... *G01N 33/4925* (2013.01); *A61K 51/025* (2013.01); *A61K 51/0402* (2013.01); *G01N 2800/2821* (2013.01); *G01N 2800/7014* (2013.01); *G01N 2800/7019* (2013.01); *G01N 2800/7028* (2013.01); *G01N 2800/7038* (2013.01); *G01N 2800/7095* (2013.01)

(58) Field of Classification Search
  CPC .............. A61K 51/025; A61K 51/0402; A61K 51/0478; G01N 33/4925; G01N 2800/7014; G01N 2800/7038; G01N 2800/2821
  See application file for complete search history.

(56) References Cited

U.S. PATENT DOCUMENTS

2018/0369428 A1   12/2018   Yoo et al.

FOREIGN PATENT DOCUMENTS

KR   10-2015-0116421 A     10/2015
KR       20170138158      * 12/2017  ............ G01N 33/60

OTHER PUBLICATIONS

Hauser, Radiology, 1969, 92(6), abstract. (Year: 1969).*
KR 2017-0138158, English translation. (Year: 2017).*
Martin et al., Dalton Trans., 2003, p. 3041-3045. (Year: 2003).*
Ang et al., "Measuring free tissue sulfide," *Adv Biol Chem. 2.4*: 360-365, Nov. 2012.
Bhatia et al., "Hydrogen sulphide is a mediator of carrageenan-induced hindpaw oedema in the rat," *Br J Pharmacol. 145.2*: 141-144, May 2005.
Cao et al., "Chemiluminescent Probes for Imaging H 2 S in Living Animals," *Chem Sci. 6.3*: 1979-1985, Mar. 2015.
Chen et al., "A ratiometric fluorescent probe for rapid detection of hydrogen sulfide in mitochondria," *Angew Chem Int Ed Engl. 52.6*: 1688-1691, Feb. 2013.
Hammers et al., "A Bright Fluorescent Probe for H2S Enables Analyte-Responsive, 3D Imaging in Live Zebrafish Using Light Sheet Fluorescence Microscopy," *J Am Chem Soc. 137.32*: 10216-10223, Aug. 2015.
Hauser et al., "Lymph node scanning with 99mTc-sulfur colloid," *Radiology 92.6*: 1369-1371, May 1969.
International Search Report and Written Opinion for PCT/KR2019/011848, mailed on Dec. 24, 2019, ISA Korean Intellectual Property Office, 9 pages (w/English translation of International Search Report, 3 pages).
Jeong et al., "Imaging of endogenous hydrogen sulfide using [99mTc]gluconate," *J Nucl Med. 60.Supplement 1*: 1082, May 2019.
Johnson et al., "99mTc-glucarate imaging for the early detection of infarct in partially reperfused canine myocardium," *European Journal of Nuclear Medicine and Molecular Imaging 33.3*: 319-328, Mar. 2006.

(Continued)

*Primary Examiner* — Michael G. Hartley
*Assistant Examiner* — Leah H Schlientz
(74) *Attorney, Agent, or Firm* — Klarquist Sparkman, LLP

(57) ABSTRACT

The present invention relates to a composition for detecting hydrogen sulfide or measuring a concentration of hydrogen sulfide, and a composition comprising same as an effective ingredient for diagnosing or imaging in vivo inflammation, tissues having hypoxic damage, or cancer. The composition for detecting hydrogen sulfide or measuring a concentration of hydrogen sulfide according to the present invention, which comprises the compound represented by formula 1 ($^{99m}$Tc-alpha-hydroxy acid) having alpha-hydroxy acid labeled with $^{99m}$Tc, enables the detection or concentration measurement of hydrogen sulfide in in-vitro and in-vivo levels and, as such, can be advantageously used for detecting hydrogen sulfide and measuring a concentration of hydrogen sulfide and furthermore for discovering biological roles of hydrogen sulfide in vivo, especially, for detecting, imaging, and quantitatively measuring hydrogen sulfide in a disease selected from the group consisting of angiogenesis, inflammation, cancer, Alzheimer's disease, cardiovascular ischemia, and cerebrovascular ischemia, or in hypoxic tissues.

14 Claims, 11 Drawing Sheets

(56) References Cited

OTHER PUBLICATIONS

Koizumi et al., "Experimental studies of ischemic brain edema 1. A new experimental model of cerebral embolism in rats in which recirculation can be introduced in the ischemic area," *Jpn J. Stroke* 8:1-8, 1986 (w/ English abstract).

Kumar et al., "Recent developments of fluorescent probes for the detection of gasotransmitters (NO, CO and H2S)," *Coordination Chemistry Reviews 257*: 2335-2347, 2013.

Lele, "Tc-99m glucoheptonate is poor man's fluorodeoxyglucose," *Indian Journal of Nuclear Medicine 26.4*: 165-170, 2011.

Li et al., "Hydrogen sulfide is a novel mediator of lipopolysaccharide-induced inflammation in the mouse," *FASEB J. 19.9*: 1196-1198, Jul. 2005.

Lippert et al., "Reaction-based fluorescent probes for selective imaging of hydrogen sulfide in living cells," *Am Chem Soc. 133.26*: 10078-10080, Jul. 2011.

Olson et al., "Controversies and conundrums in hydrogen sulfide biology," *Nitric Oxide 41*: 11-26, Sep. 2014.

Ren et al., "Dynamic change of hydrogen sulfide during global cerebral ischemia-reperfusion and its effect in rats," *Brain Res. 1345*: 194-205, Jul. 2010.

Sarkar et al., "Immobilization of the Gas Signaling Molecule H2S by Radioisotopes: Detection, Quantification, and In Vivo Imaging," *Angew Chem Int Ed Engl. 55.32*: 9365-9370, Aug. 2016.

Sasakura et al., "Development of a highly selective fluorescence probe for hydrogen sulfide," *Am Chem Soc. 133.45*: 18003-18005, Nov. 2011.

"Technical Reports Series No. 466: Technetium-99m Radiopharmaceuticals: Manufacture of Kits," International Atomic Energy Agency, Vienna, Aug. 2008 (202 pages).

Ballinger et al., "Effect of Hypoxia on the Accumulation of Technetium-99m-Glucarate and Technetium-99m-Gluconate by Chinese Hamster Ovary Cells in Vitro," *J Nucl Med. 34.2*: 242-245, Feb. 1, 1993.

Kowalsky, "Technetium Radiopharmaceutical Chemistry: Continuing Education for Nuclear Pharmacists and Nuclear Medicine Professionals," The University of New Mexico Health Sciences Center College of Pharmacy 12.3: 1-77, 2006.

"7.5: Preparation of Kit for 99mTc-Glucoheptonate," *Technical Reports Series No. 466: Technetium-99m Radiopharmaceuticals: Manufacture of Kits*, International Atomic Energy Agency, Vienna, pp. 77-78, Aug. 2008.

Gambini, Juan Pablo et al., "Evaluation of $^{99m}$Tc-glucarate as a breast cancer imaging agent in a xenograft animal model," *Nuclear Medicine and Biology*, 38(2):255-260 (Feb. 2011).

\* cited by examiner

FIG. 10
 

FIG. 11
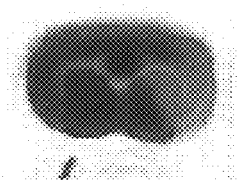 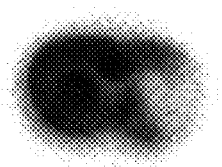 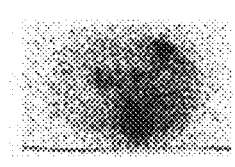
TTC  [$^{18}$F]FDG  [$^{99m}$Tc]Gluconate

COMPOSITION FOR DETECTING HYDROGEN SULFIDE OR MEASURING HYDROGEN SULFIDE CONCENTRATION AND COMPOSITION COMPRISING SAME AS EFFECTIVE INGREDIENT FOR DIAGNOSING OR IMAGING IN VIVO INFLAMMATION, TISSUES HAVING HYPOXIC DAMAGE, OR CANCER

CROSS-REFERENCE TO RELATED APPLICATIONS

This is the U.S. National Stage of International Application No. PCT/KR2019/011848, filed Sep. 11, 2019, which in turn claims the benefit of priority from Korean Application No. 10-2018-0108234, filed Sep. 11, 2018. The contents of each of which are herein incorporated by reference in their entirety.

BACKGROUND OF THE INVENTION

1. Field of the Invention

The present invention relates to a composition for detecting hydrogen sulfide or measuring a concentration of hydrogen sulfide, and a composition comprising the same as an active ingredient for diagnosing or imaging in vivo inflammation, tissues having hypoxic damage, or cancer.

2. Description of the Related Art

Hydrogen sulfide gas is caused by rotting proteins such as eggs and is famous for its bad smell. This gas is mainly generated from natural volcanoes, soil or water resources contaminated with organic matters, and may be generated from living organisms in a normal or disease status. In addition, hydrogen sulfide has been found to improve or worsen disease status depending on the type of disease in the animal body. Therefore, it is necessary to detect and quantify hydrogen sulfide in order to measure the pollution level of natural soil, air, and water resources, or to diagnose disease conditions in a living body.

In addition, hydrogen sulfide has been reported to be associated with numerous diseases such as various inflammatory responses in the human body, hypoxia, cardiovascular disease, stroke, angiogenesis, vasodilation, cancer, Down's syndrome, dementia, diabetes, and Huntington's disease. Therefore, its detection is very important for diagnosing various diseases and predicting the prognosis.

Accordingly, many methods such as methylene blue method, ion selective electrode method, monobromo obimane-HPLC method, thiobromobimane-GC method, and current detection method have been developed and reported to measure the hydrogen sulfide concentration in a sample (KR Olson, et al., Nitric Oxide (2014) 41; 11-26). However, since these methods simply measure the concentration of hydrogen sulfide in samples such as blood, it is impossible to know its distribution more accurately.

A method for detecting hydrogen sulfide by fluorescence was developed, making it possible to show the hydrogen sulfide generation site in an image. However, fluorescence is weak in permeability, so it cannot be used to detect or image hydrogen sulfide generated in humans or large animals. It can only be used to detect and image hydrogen sulfide generation in very small animals such as mouse and zebrafish, or in intracellular organs such as mitochondria (MD Hammers, et al., J Am Chem Soc (2015) 137:10216-10223; Y Chen, et al., Angew Chem Int Ed (2013) 52:1688-1691; K Sasakura, et al., J Am Chem Soc (2011) 133:18003-18005; AR Lippert, et al., J Am Chem Soc (2011) 133: 10078-10080; N Kumar, et al., Coord Chem Rev (2013) 257:2335-2347).

A method of detection by low-temperature chemiluminescence has also been developed, but this method has a problem that is applicable only to small animals (J Cao, et al., Chem Sci (2015) 6:1979-1985).

Recently, a method for detecting hydrogen sulfide using a radioactive isotope that emits radiation with strong penetrating power has been developed. In this method, $^{64}$Cu emitting positrons combines with hydrogen sulfide to form insoluble $^{64}$CuS and deposits on the hydrogen sulfide generation site to detect and image the radioactivity at this site (S Sarkar, et al., Angew Chem Int Ed (2016) 55:9365-9370; Korean Patent Publication No. 10-2017-0018121). The above method can image the hydrogen sulfide generation site deep in the human body with high resolution using PET (Positron Emission Tomography). However, since Cu-64 should be made by proton irradiation of Ni-64, an expensive target material, using an expensive cyclotron, the price is very expensive and there are many restrictions in use.

SUMMARY OF THE INVENTION

It is an object of the present invention to provide a composition for detecting hydrogen sulfide or measuring a concentration of hydrogen sulfide.

It is another object of the present invention to provide a composition for diagnosing or imaging inflammation, tissues having hypoxic damage, or cancer.

To achieve the above objects, in one aspect of the present invention, a composition for detecting hydrogen sulfide comprising a compound represented by formula 1 having alpha-hydroxy acid labeled with $^{99m}$Tc is provided:

(In formula 1,
$R^1$ and $R^2$ are independently hydrogen or —OH; and
m is an integer of 0~20).

In another aspect of the present invention, a preparation method of a composition for detecting hydrogen sulfide comprising a compound represented by formula 1 having alpha-hydroxy acid labeled with $^{99m}$Tc, containing a step of reacting $^{99m}$Tc with the alpha-hydroxy acid represented by formula 2 or an alkali metal or alkaline earth metal salt thereof is provided:

(In formula 1,
$R^1$ and $R^2$ are independently hydrogen or —OH; and
m is an integer of 0~20);

(In formula 2,
$R^1$ and $R^2$ are independently hydrogen or —OH; and
m is an integer of 0~20).

In another aspect of the present invention, a composition for measuring a concentration of hydrogen sulfide comprising a compound represented by formula 1 having alpha-hydroxy acid labeled with $^{99m}$Tc is provided:

(In formula 1,
$R^1$ and $R^2$ are independently hydrogen or —OH; and
m is an integer of 0~20).

In another aspect of the present invention, a composition for imaging a disease in which hydrogen sulfide is generated, comprising a compound represented by formula 1 is provided:

$$O—^{99m}Tc(O=CO^-—CHO^-—(CHR^1)_m—CH_2R^2)_2 \quad \text{[Formula 1]}$$

(In formula 1,
R is independently hydrogen or hydroxyl group; and
m is an integer of 0~20).

In another aspect of the present invention, a composition for diagnosing a disease in which hydrogen sulfide is generated, comprising a compound represented by formula 1 is provided:

$$O=^{99m}Tc(O=CO^-—CHO^-—(CHR^1)_m—CH_2R^2)_2 \quad \text{[Formula 1]}$$

(In formula 1,
R is independently hydrogen or hydroxyl group; and
m is an integer of 0~20).

In another aspect of the present invention, a kit for preparing a compound represented by formula 1 comprising the alpha-hydroxy acid represented by formula 2 or an alkali metal or alkaline earth metal salt thereof and an adjuvant is provided:

$$O—^{99m}Tc(O=CO^-—CHO^-—(CHR^1)_m—CH_2R^2)_2 \quad \text{[Formula 1]}$$

(In formula 1,
R is independently hydrogen or hydroxyl group; and
m is an integer of 0~20).

$$HOOC—CHOH—(CHR^1)_m—CH_2R^2 \quad \text{[Formula 2]}$$

(In formula 2,
$R^1$ and $R^2$ are independently hydrogen or —OH; and
m is an integer of 0~20).

Advantageous Effect

The composition for detecting hydrogen sulfide or measuring a concentration of hydrogen sulfide according to the present invention, which comprises the compound represented by formula 1 ($^{99m}$Tc-alpha-hydroxy acid) having alpha-hydroxy acid labeled with $^{99m}$Tc, enables the detection or concentration measurement of hydrogen sulfide in in-vitro and in-vivo levels and, as such, can be advantageously used for detecting hydrogen sulfide and measuring a concentration of hydrogen sulfide and furthermore for discovering biological roles of hydrogen sulfide in vivo, especially, for detecting, imaging, and quantitatively measuring hydrogen sulfide in a disease selected from the group consisting of angiogenesis, inflammation, cancer, Alzheimer's disease, cardiovascular ischemia, and cerebrovascular ischemia, or in hypoxic tissues.

BRIEF DESCRIPTION OF THE DRAWINGS

FIG. 10 is a set of SPECT/CT images obtained 1 hour after the administration of carrageenan to the sole of a mouse to induce inflammation and physiological saline to the other food and then $^{99m}$Tc-gluconate and $^{99m}$Tc-glucoheptonate performed in Experimental Example 5.

FIG. 11 is a set of images of the rat brain extracted, autoradiated and TTC stained 1 hour after the middle cerebral artery of a rat was occluded for 2 hours, reperfused, and administered with $^{99m}$Tc-gluconate and [$^{18}$F]FDG simultaneously performed in Experimental Example 6.

DESCRIPTION OF THE PREFERRED EMBODIMENTS

Figure 1:
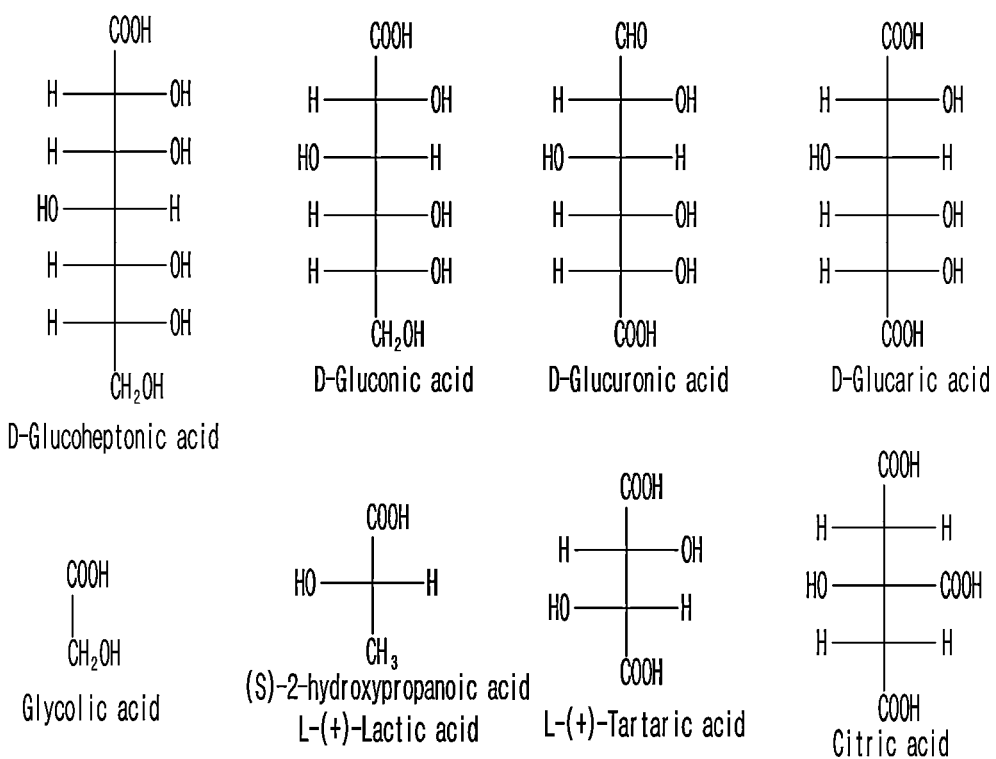
FIG. 1 is a diagram showing the formula of alpha-hydroxy acid.
Figure 2:
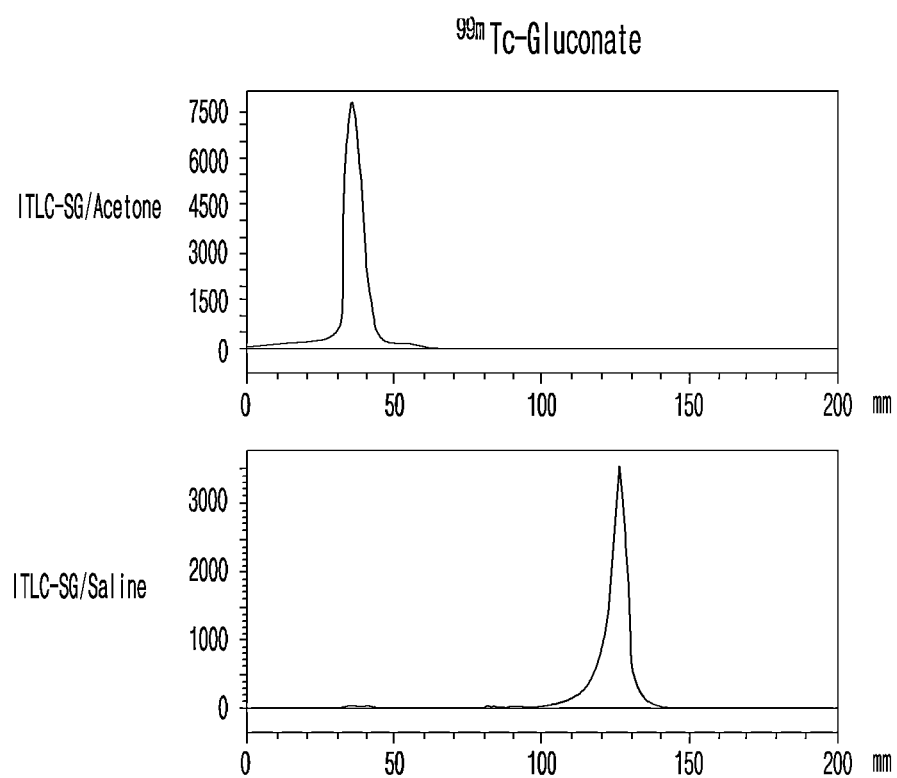
FIG. 2 is a set of graphs showing the results of measuring labeling efficiency by developing the $^{99m}$Tc-gluconate labeled with $^{99m}$Tc according to the method of Example 1 using D-gluconate as alpha-hydroxy acid by ITLC-SG using acetone and physiological saline.
Figure 3:
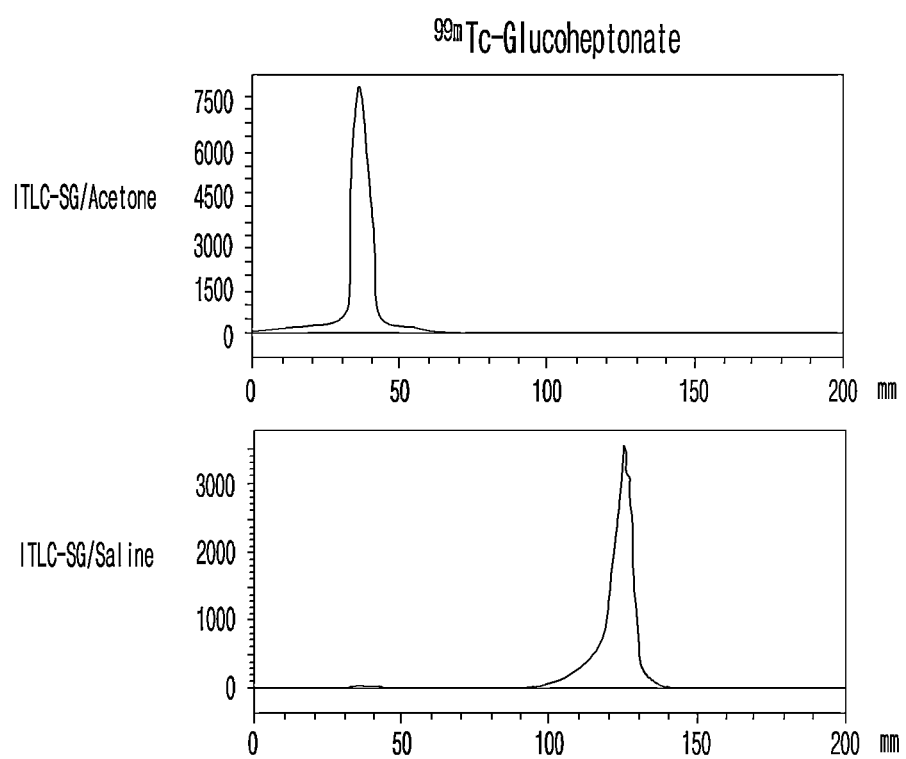
FIG. 3 is a set of graphs showing the results of measuring labeling efficiency by developing the $^{99m}$Tc-glucoheptonate labeled with $^{99m}$Tc according to the method of Example 1 using D-glucoheptonate as alpha-hydroxy acid by ITLC-SG using acetone and physiological saline.
Figure 4:
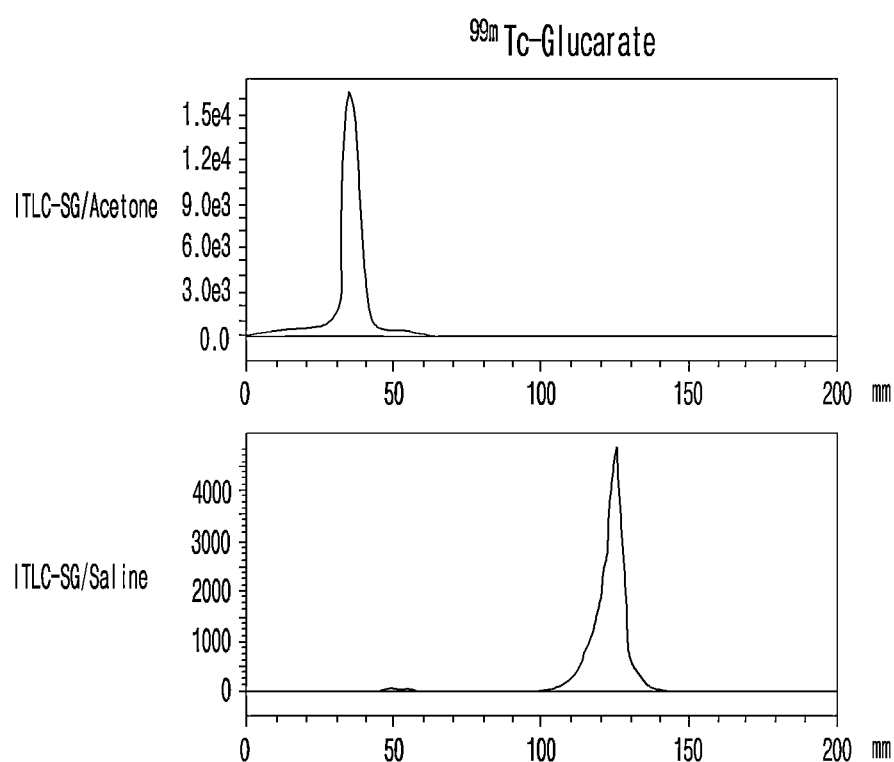
FIG. 4 is a set of graphs showing the results of measuring labeling efficiency by developing the $^{99m}$Tc-glucarate labeled with $^{99m}$Tc according to the method of Example 1 using D-glucarate as alpha-hydroxy acid by ITLC-SG using acetone and physiological saline.
Figure 5:
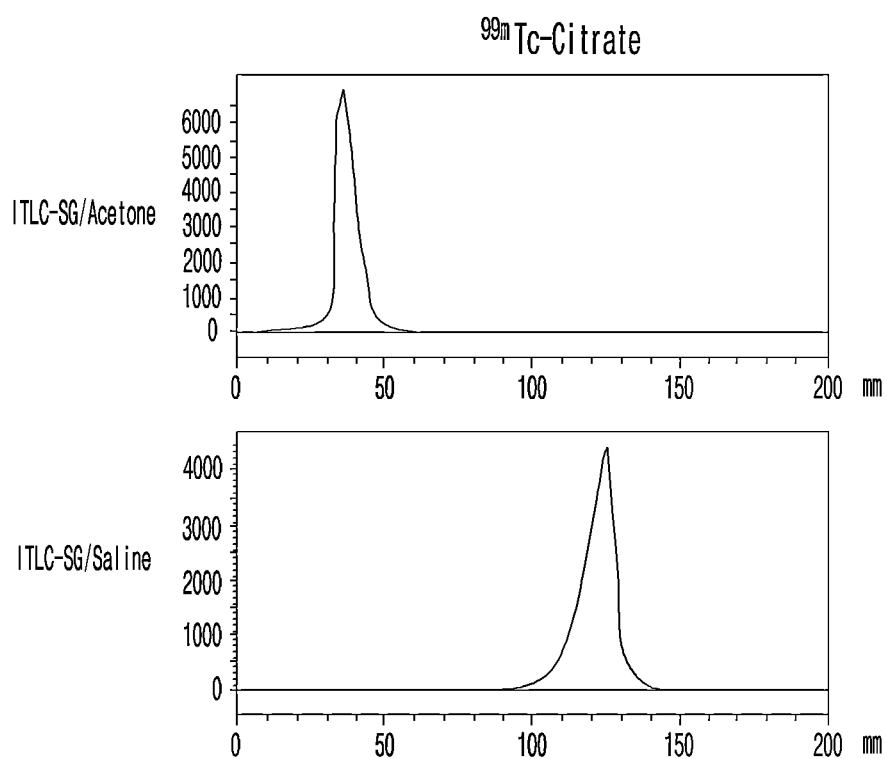
FIG. 5 is a set of graphs showing the results of measuring labeling efficiency by developing the $^{99m}$Tc-citrate labeled with $^{99m}$Tc according to the method of Example 1 using citrate as alpha-hydroxy acid by ITLC-SG using acetone and physiological saline.
Figure 6:
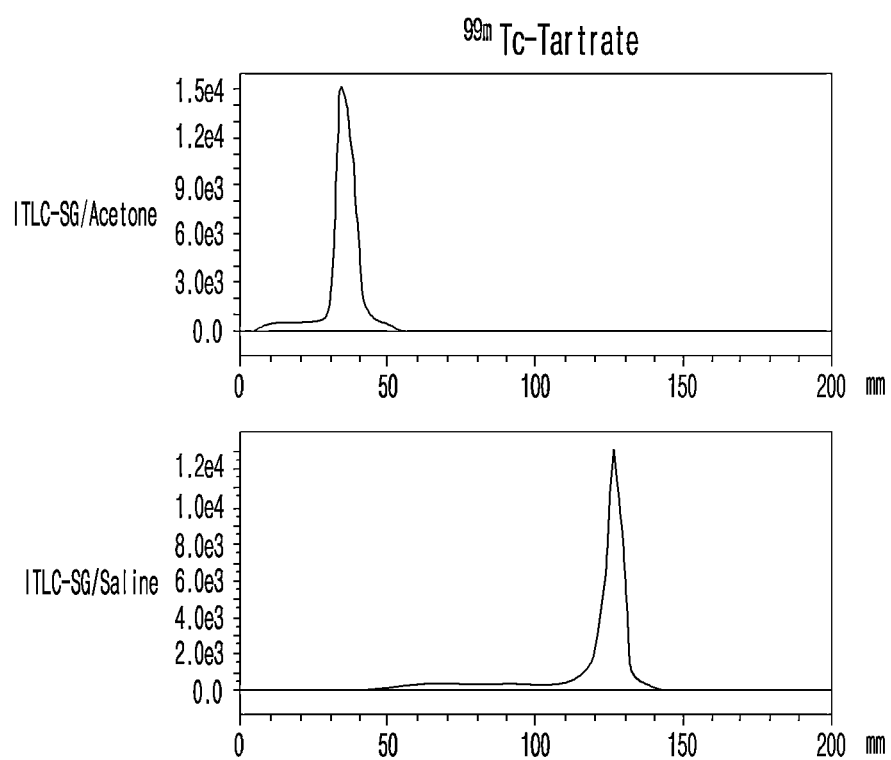
FIG. 6 is a set of graphs showing the results of measuring labeling efficiency by developing the $^{99m}$Tc-tartrate labeled with $^{99m}$Tc according to the method of Example 1 using L-tartrate as alpha-hydroxy acid by ITLC-SG using acetone and physiological saline.
Figure 7:
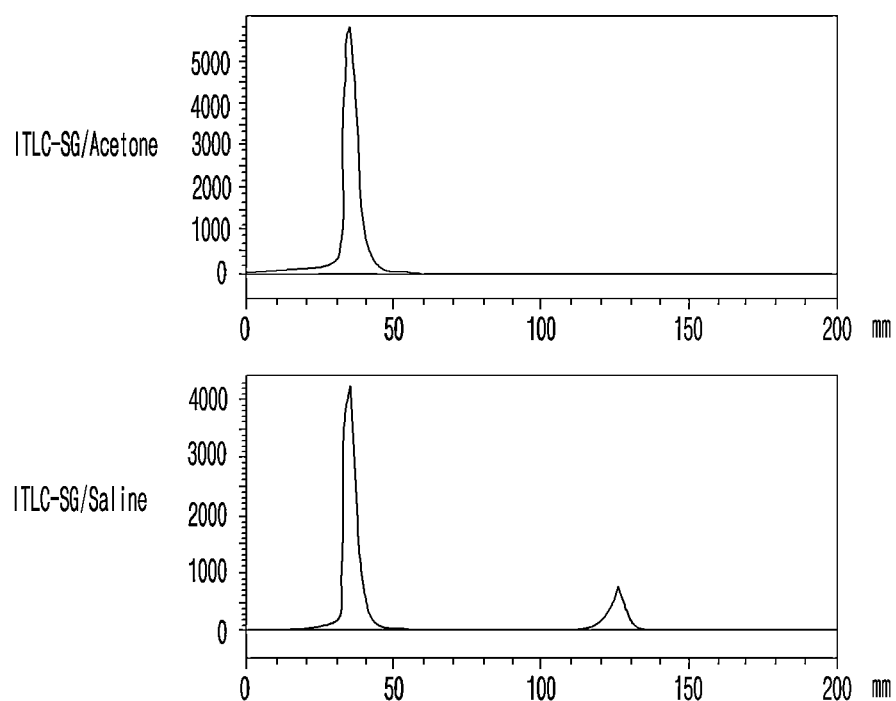
FIG. 7 is a set of graphs showing the results of measuring labeling efficiency by developing the $^{99m}$Tc-glucuronate labeled with $^{99m}$Tc according to the method of Example 1 using D-glucuronate as alpha-hydroxy acid by ITLC-SG using acetone and physiological saline.

In one aspect of the present invention, a composition for detecting hydrogen sulfide comprising a compound represented by formula 1 having alpha-hydroxy acid labeled with $^{99m}$Tc is provided:

$$O=^{99m}Tc(O=CO^-—CHO^-—(CHR^1)_m—CH_2R^2)_2 \quad \text{[Formula 1]}$$

(In formula 1,
$R^1$ and $R^2$ are independently hydrogen or —OH; and
m is an integer of 0~20).

The alpha-hydroxy acid can be a compound represented by formula 2 below.

$$HOOC—CHOH—(CHR^1)_m—CH_2R^2 \quad \text{[Formula 2]}$$

(In formula 2,
$R^1$ and $R^2$ are independently hydrogen or —OH; and
m is an integer of 0~20).

In addition, the alpha-hydroxy acid can be selected from the group consisting of D-gluconic acid, D-glucoheptonic acid, galactonic acid, D-glucaric acid, tartaric acid, citric acid, glycolic acid, D-lactic acid, L-lactic acid and D-glucuronic acid.

The composition for detecting hydrogen sulfide reacts with hydrogen sulfide to form an insoluble material, thereby enabling imaging. Thus, it can be used to detect hydrogen sulfide.

The composition for detecting hydrogen sulfide can detect hydrogen sulfide in the tissues or cells isolated from animal subjects.

The tissue or cell can be a tissue or cell in which hydrogen sulfide has been generated, or a tissue or cell of a disease selected from the group consisting of angiogenesis, inflammation, cancer, Alzheimer's dementia, cardiovascular ischemia, cerebrovascular ischemia and hypoxia in which hydrogen sulfide has been generated. In addition, the tissue or cell can be a tissue or cell of a disease selected from the group consisting of rheumatoid arthritis, non-rheumatic inflammatory arthritis, arthritis related to Lyme disease, pyelonephritis, nephritis, inflammatory osteoarthritis, meningitis, osteomyelitis, inflammatory bowel disease, appendicitis, pancreatitis, sepsis, inflammatory disease due to bacterial infection, myocardial infarction, heart ischemia, angina, angina pectoris, cardiomyopathy, endocarditis, arteriosclerosis, sepsis, diabetes, stroke, cirrhosis, asthma, Parkinson's disease, Alzheimer's disease, dementia, Down's syndrome, lung cancer, breast cancer, uterine cancer, ovarian cancer, liver cancer, brain cancer, prostate cancer, thyroid cancer, neuroendocrine tumor, stomach cancer, colon cancer, pancreatic cancer, bladder cancer, esophageal cancer and head/neck cancer.

The composition for detecting hydrogen sulfide can detect hydrogen sulfide in a disease selected from the group consisting of angiogenesis, inflammation, cancer, Alzheimer's dementia, cardiovascular ischemia, cerebrovascular ischemia and hypoxia. At this time, the disease can be a hydrogen sulfide-generated disease or hypoxic tissue.

Since the composition for detecting hydrogen sulfide of the present invention selectively detects only NaHS (hydrogen sulfide) among active sulfides, it can be effectively used for the detection of hydrogen sulfide (Experimental Example 2).

In another aspect of the present invention, the present invention provides a preparation method of a composition for detecting hydrogen sulfide comprising a compound represented by formula 1 having alpha-hydroxy acid labeled with $^{99m}$Tc, containing a step of reacting $^{99m}$Tc with the alpha-hydroxy acid represented by formula 2 or an alkali metal or alkaline earth metal salt thereof.

$$O=^{99m}Tc(O=CO^--CHO^--(CHR^1)_m-CH_2R^2)_2 \quad \text{[Formula 1]}$$

(In formula 1,
R$^1$ and R$^2$ are independently hydrogen or —OH; and
m is an integer of 0~20);

$$HOOC-CHOH-(CHR^1)_m-CH_2R^2 \quad \text{[Formula 2]}$$

(In formula 2,
R$^1$ and R$^2$ are independently hydrogen or —OH; and
m is an integer of 0~20).

The alpha-hydroxy acid represented by formula 2 can be selected from the group consisting of D-gluconic acid, D-glucoheptonic acid, galactonic acid, D-glucaric acid, tartaric acid, citric acid, glycolic acid, D-lactic acid, L-lactic acid and D-glucuronic acid.

The alkali metal can be selected from the group consisting of lithium (Li), sodium (Na), potassium (K), rubidium (Rb) and cesium (Cs).

The alkaline earth metal can be selected from the group consisting of magnesium (Mg), calcium (Ca), strontium (Sr) and barium (Ba).

Specifically, the preparation method above is a method to obtain $^{99m}$Tc-labeled alpha-hydroxy acid, that is, a compound represented by formula 1, by synthesizing a technetium complex on the alpha-hydroxy acid represented by formula 2.

In the preparation method of the present invention, $^{99m}$Tc generated in a generator was used, but $^{99m}$Tc immediately released from the generator was present as a very stable form of pertechnetic acid with an oxidation number of +7, and thus was not labeled. Therefore, it is necessary to decrease the oxidation number by reducing it. At this time, the reducing agent can be used without limitation, as long as it is a commonly used reducing agent. In one embodiment of the present invention, SnCl$_2$ was used as the reducing agent, but not always limited thereto.

In order to easily and conveniently label the alpha-hydroxy acid with $^{99m}$Tc, stabilizers, excipients or buffers can further be used as other additives. SnCl$_2$, ascorbic acid, gentisinic acid, calcium chloride, sodium chloride, sodium phosphate, mannitol, glucose, lactose, sodium ascorbate, and the like can be used as the other additives.

The preparation method according to the present invention was able to label the alpha-hydroxy acid with $^{99m}$Tc with a labeling efficiency of almost 100% (Experimental Example 1).

In another aspect of the present invention, the present invention provides a composition for measuring a concentration of hydrogen sulfide comprising a compound represented by formula 1 having alpha-hydroxy acid labeled with $^{99m}$Tc.

$$O=^{99m}Tc(O=CO^--CHO^--(CHR^1)_m-CH_2R^2)_2 \quad \text{[Formula 1]}$$

(In formula 1,
R$^1$ and R$^2$ are independently hydrogen or —OH; and
m is an integer of 0~20).

The alpha-hydroxy acid can be a compound represented by formula 2 below.

$$HOOC-CHOH-(CHR^1)_m-CH_2R^2 \quad \text{[Formula 2]}$$

(In formula 2,
R$^1$ and R$^2$ are independently hydrogen or —OH; and
m is an integer of 0~20).

In addition, the alpha-hydroxy acid represented by formula 2 can be selected from the group consisting of D-gluconic acid, D-glucoheptonic acid, galactonic acid, D-glucaric acid, tartaric acid, citric acid, glycolic acid, D-lactic acid, L-lactic acid and D-glucuronic acid.

The composition for measuring a concentration of hydrogen sulfide reacts with hydrogen sulfide to form an insoluble material, so that the concentration of hydrogen sulfide can be measured.

The composition for measuring a concentration of hydrogen sulfide can measure the concentration of hydrogen sulfide in the tissues or cells isolated from animal subjects.

The tissue or cell can be a tissue or cell in which hydrogen sulfide has been generated, or a tissue or cell of a disease selected from the group consisting of angiogenesis, inflammation, cancer, Alzheimer's dementia, cardiovascular ischemia, cerebrovascular ischemia and hypoxia in which hydrogen sulfide has been generated. In addition, the tissue or cell can be a tissue or cell of a disease selected from the group consisting of rheumatoid arthritis, non-rheumatic inflammatory arthritis, arthritis related to Lyme disease, pyelonephritis, nephritis, inflammatory osteoarthritis, meningitis, osteomyelitis, inflammatory bowel disease, appendicitis, pancreatitis, sepsis, inflammatory disease due to bacterial infection, myocardial infarction, heart ischemia, angina, angina pectoris, cardiomyopathy, endocarditis, arteriosclerosis, sepsis, diabetes, stroke, cirrhosis, asthma, Parkinson's disease, Alzheimer's disease, dementia, Down's syndrome, lung cancer, breast cancer, uterine cancer, ovarian cancer, liver cancer, brain cancer, prostate cancer, thyroid cancer, neuroendocrine tumor, stomach cancer, colon cancer, pancreatic cancer, bladder cancer, esophageal cancer and head/neck cancer.

The composition for measuring a concentration of hydrogen sulfide can detect hydrogen sulfide in a disease selected from the group consisting of angiogenesis, inflammation, cancer, Alzheimer's dementia, cardiovascular ischemia, cerebrovascular ischemia and hypoxia. At this time, the disease can be a hydrogen sulfide-generated disease or hypoxic tissue.

The composition for measuring a concentration of hydrogen sulfide can be effectively used for measuring the concentration of hydrogen sulfide since the degree of formation of an insoluble substance changes according to the concentration of hydrogen sulfide (Experimental Example 3).

In another aspect of the present invention, the present invention provides a composition for imaging a disease in which hydrogen sulfide is generated, comprising a compound represented by formula 1.

$$O{=}^{99m}Tc(O{=}CO^-{-}CHO^-{-}(CHR^1)_m{-}CH_2R^2)_2 \quad \text{[Formula 1]}$$

(In formula 1,
R is independently hydrogen or hydroxyl group; and
m is an integer of 0~20).

The alpha-hydroxy acid can be a compound represented by formula 2 below.

$$HOOC{-}CHOH{-}(CHR^1)_m{-}CH_2R^2 \quad \text{[Formula 2]}$$

(In formula 2,
$R^1$ and $R^2$ are independently hydrogen or —OH; and
m is an integer of 0~20).

In addition, the alpha-hydroxy acid can be selected from the group consisting of D-gluconic acid, D-glucoheptonic acid, galactonic acid, D-glucaric acid, tartaric acid, citric acid, glycolic acid, D-lactic acid, L-lactic acid and D-glucuronic acid.

The composition for imaging a disease in which hydrogen sulfide is generated reacts with hydrogen sulfide to form an insoluble material, so that hydrogen sulfide can be imaged.

The disease can be selected from the group consisting of angiogenesis, inflammation, cancer, Alzheimer's dementia, cardiovascular ischemia, cerebrovascular ischemia and hypoxia.

In addition, the disease can be selected from the group consisting of rheumatoid arthritis, non-rheumatic inflammatory arthritis, arthritis related to Lyme disease, pyelonephritis, nephritis, inflammatory osteoarthritis, meningitis, osteomyelitis, inflammatory bowel disease, appendicitis, pancreatitis, sepsis, inflammatory disease due to bacterial infection, myocardial infarction, heart ischemia, angina, angina pectoris, cardiomyopathy, endocarditis, arteriosclerosis, sepsis, diabetes, stroke, cirrhosis, asthma, Parkinson's disease, Alzheimer's disease, dementia, Down's syndrome, lung cancer, breast cancer, uterine cancer, ovarian cancer, liver cancer, brain cancer, prostate cancer, thyroid cancer, neuroendocrine tumor, stomach cancer, colon cancer, pancreatic cancer, bladder cancer, esophageal cancer and head/neck cancer.

The composition for imaging a disease in which hydrogen sulfide is generated according to the present invention can image the inflamed tissue in which hydrogen sulfide is generated, and the concentration increase can be known through whether the intake of the treated composition for imaging increases, so that not only imaging but also the increase in concentration can be confirmed. In addition, since the hydrogen sulfide concentration can be quantified and expressed numerically through fluorescence assay, it can be effectively used to measure the concentration of hydrogen sulfide in the inflamed tissue (Experimental Examples 4 and 5).

In addition, from the increase in the concentration of hydrogen sulfide in reperfusion after middle cerebral artery occlusion using the composition for imaging according to the present invention, it was confirmed that hydrogen sulfide was generated in the reperfused tissue. It was also confirmed that hydrogen sulfide detection, concentration measurement, and imaging in the reperfused tissue after middle cerebral artery occlusion were possible (Experimental Example 6).

In another aspect of the present invention, the present invention provides a composition for diagnosing a disease in which hydrogen sulfide is generated, comprising a compound represented by formula 1.

$$O{=}^{99m}Tc(O{=}CO^-{-}CHO^-{-}(CHR^1)_m{-}CH_2R^2)_2 \quad \text{[Formula 1]}$$

(In formula 1,
R is independently hydrogen or hydroxyl group; and
m is an integer of 0~20).

The alpha-hydroxy acid can be a compound represented by formula 2 below.

$$HOOC{-}CHOH{-}(CHR^1)_m{-}CH_2R^2 \quad \text{[Formula 2]}$$

(In formula 2,
$R^1$ and $R^2$ are independently hydrogen or —OH; and
m is an integer of 0~20).

In addition, the alpha-hydroxy acid can be selected from the group consisting of D-gluconic acid, D-glucoheptonic acid, galactonic acid, D-glucaric acid, tartaric acid, citric acid, glycolic acid, D-lactic acid, L-lactic acid and D-glucuronic acid.

The composition for diagnosing a disease in which hydrogen sulfide is generated reacts with hydrogen sulfide to form an insoluble material, so that diagnosis of a disease in which hydrogen sulfide is generated is possible.

The disease can be selected from the group consisting of angiogenesis, inflammation, cancer, Alzheimer's dementia, cardiovascular ischemia, cerebrovascular ischemia and hypoxia.

In addition, the disease can be selected from the group consisting of rheumatoid arthritis, non-rheumatic inflammatory arthritis, arthritis related to Lyme disease, pyelonephritis, nephritis, inflammatory osteoarthritis, meningitis, osteomyelitis, inflammatory bowel disease, appendicitis, pancreatitis, sepsis, inflammatory disease due to bacterial infection, myocardial infarction, heart ischemia, angina, angina pectoris, cardiomyopathy, endocarditis, arteriosclerosis, sepsis, diabetes, stroke, cirrhosis, asthma, Parkinson's disease, Alzheimer's disease, dementia, Down's syndrome, lung cancer, breast cancer, uterine cancer, ovarian cancer, liver cancer, brain cancer, prostate cancer, thyroid cancer, neuroendocrine tumor, stomach cancer, colon cancer, pancreatic cancer, bladder cancer, esophageal cancer and head/neck cancer.

The composition for diagnosing a disease in which hydrogen sulfide is generated according to the present invention can image the inflamed tissue in which hydrogen sulfide is generated, and the concentration increase can be known through whether the intake of the treated composition for imaging increases, so that not only imaging but also the increase in concentration can be confirmed. In addition, since the hydrogen sulfide concentration can be quantified and expressed numerically through fluorescence assay, it can be effectively used not only for diagnosing inflammatory disease, but also for assessing progression (Experimental Example 5).

In addition, from the increase in the concentration of hydrogen sulfide in reperfusion after middle cerebral artery occlusion using the composition for imaging according to the present invention, it was confirmed that hydrogen sulfide was generated in the reperfused tissue. It was also confirmed that the reperfused tissue can be diagnosed after the middle cerebral artery occlusion (Experimental Example 6).

In another aspect of the present invention, the present invention provides a kit for preparing a compound represented by formula 1 comprising the alpha-hydroxy acid represented by formula 2 or an alkali metal or alkaline earth metal salt thereof and an adjuvant:

  [Formula 1]

(In formula 1,
R is independently hydrogen or hydroxyl group; and
m is an integer of 0~20).

  [Formula 2]

(In formula 2,
$R^1$ and $R^2$ are independently hydrogen or —OH; and
m is an integer of 0~20).

The alpha-hydroxy acid represented by formula 2 can be selected from the group consisting of D-gluconic acid, D-glucoheptonic acid, galactonic acid, D-glucaric acid, tartaric acid, citric acid, glycolic acid, D-lactic acid, L-lactic acid and D-glucuronic acid.

The adjuvant can be at least one selected from the group consisting of $SnCl_2$, ascorbic acid, gentisinic acid, calcium chloride, sodium chloride, sodium phosphate, mannitol, glucose, lactose and sodium ascorbate.

The alkali metal can be selected from the group consisting of lithium (Li), sodium (Na), potassium (K), rubidium (Rb) and cesium (Cs).

The alkaline earth metal can be selected from the group consisting of magnesium (Mg), calcium (Ca), strontium (Sr) and barium (Ba).

The kit can include an adjuvant for easy and convenient labeling of alpha-hydroxy acid with $^{99m}Tc$. The adjuvant can be a stabilizer, an excipient or a buffering agent, and specifically, as the other additives, $SnCl_2$, ascorbic acid, gentisinic acid, calcium chloride, sodium chloride, sodium phosphate, mannitol, glucose, lactose, sodium ascorbate, and the like can be used.

Specifically, the kit can be a freeze-dried kit including the alpha-hydroxy acid represented by formula 2 or an alkali metal or alkaline earth metal salt thereof and a reducing agent such as tin chloride as an adjuvant. At this time, in order to optimize the labeling efficiency, the kit can be prepared by adjusting the pH inside the kit to 3~10, preferably 4~7.

$^{99m}Tc$ is added to the kit so that it can be used by labeling alpha-hydroxy acid with $^{99m}Tc$ within 1 hour at room temperature ~100° C.

The kit can additionally contain an antioxidant and an excipient. At this time, the antioxidant is to prevent deterioration of the alpha-hydroxy acid labeled with a radioactive isotope by oxidation or radiolysis. Vitamin C or gentisic acid can be used as the antioxidant. The antioxidant and excipient can be contained about 0 to 500 mg per unit dosage of the kit.

The kit can be frozen or lyophilized in a sterilization container under inert gas environment. The kit can further include buffer sterilization vials, saline, syringes, filters, columns, and other auxiliary devices to prepare injections for use in hospitals. Such modifications are well known to those having ordinary skills in the art.

The kit can be used by labeling $^{99m}Tc$ within 1 hour at room temperature ~100° C.

The composition for detecting hydrogen sulfide or measuring a concentration of hydrogen sulfide according to the present invention, which comprises the compound represented by formula 1 ($^{99m}Tc$-alpha-hydroxy acid) having alpha-hydroxy acid labeled with $^{99m}Tc$, enables the detection or concentration measurement of hydrogen sulfide in in-vitro and in-vivo levels and, as such, can be advantageously used for detecting hydrogen sulfide and measuring a concentration of hydrogen sulfide and furthermore for discovering biological roles of hydrogen sulfide in vivo, especially, for detecting, imaging, and quantitatively measuring hydrogen sulfide in a disease selected from the group consisting of angiogenesis, inflammation, cancer, Alzheimer's disease, cardiovascular ischemia, and cerebrovascular ischemia, or in hypoxic tissues.

In addition, $^{99m}Tc$ is easier to supply than other radioactive isotopes and is competitive in price, so it has an economic advantage.

Hereinafter, the present invention will be described in detail by the following examples and experimental examples.

However, the following examples and experimental examples are only for illustrating the present invention, and the contents of the present invention are not limited thereto.

Example 1: Preparation of $^{99m}Tc$-Labeled Alpha-Hydroxy Acid ($^{99m}Tc$-Alpha-Hydroxy Acid)

D-gluconate, D-glucoheptonate, D-glucarate, citrate, L-tartrate, and D-glucuronate were selected as the alpha-hydroxy acid, and each alpha-hydroxy acid was labeled with $^{99m}Tc$ by the following method. All distilled water used for labeling was used after blowing with nitrogen gas for 1 hour. 10 μL of sodium ascorbate (25 mg/mL) was added to 100 μL of each 0.3 M alpha-hydroxy acid, to which 50 μL of $SnCl_2 \cdot 2H_2O$ (2.5 mg/mL in 0.05 M HCl) was added, followed by mixing well. 140 μL of $^{99m}Tc$ (3 mCi) obtained from the generator was added thereto, which was placed at room temperature for 20 minutes, or heated at 100° C. for 10 minutes to label.

Experimental Example 1: Measurement of Labeling Efficiency

In order to measure the labeling efficiency of the $^{99m}Tc$-labeled alpha-hydroxy acid ($^{99m}Tc$-alpha-hydroxy acid) prepared in Example 1, the following experiment was performed. The results of measuring the labeling efficiency of each $^{99m}Tc$-alpha-hydroxy acid are shown in FIGS. 2~7.

Particularly, the labeling efficiency was measured by ITLC (Instant Thin Layer Chromatography). After loading 1 to 5 μL of the sample at a position of 1 cm from the bottom of an ITLC plate having a length of 10 cm and a width of 1 cm, the plate was placed in a developing tank containing acetone or physiological saline and developed. Upon completion of the deployment, radioactivity was scanned using a Radio-TLC scanner. At this time, when developed with acetone, only the unlabeled $^{99m}Tc$ went up along the solvent, and the labeled $^{99m}Tc$ and the colloidal $^{99m}Tc$ remained at the origin. When developed with physiological saline, the colloidal $^{99m}Tc$ remained at the origin, and the unlabeled $^{99m}Tc$ and the labeled $^{99m}Tc$ went up along the solvent.

As shown in FIGS. 2~7, almost 100% of the labeling efficiency was shown for all alpha-hydroxy acids.

Figure 8:
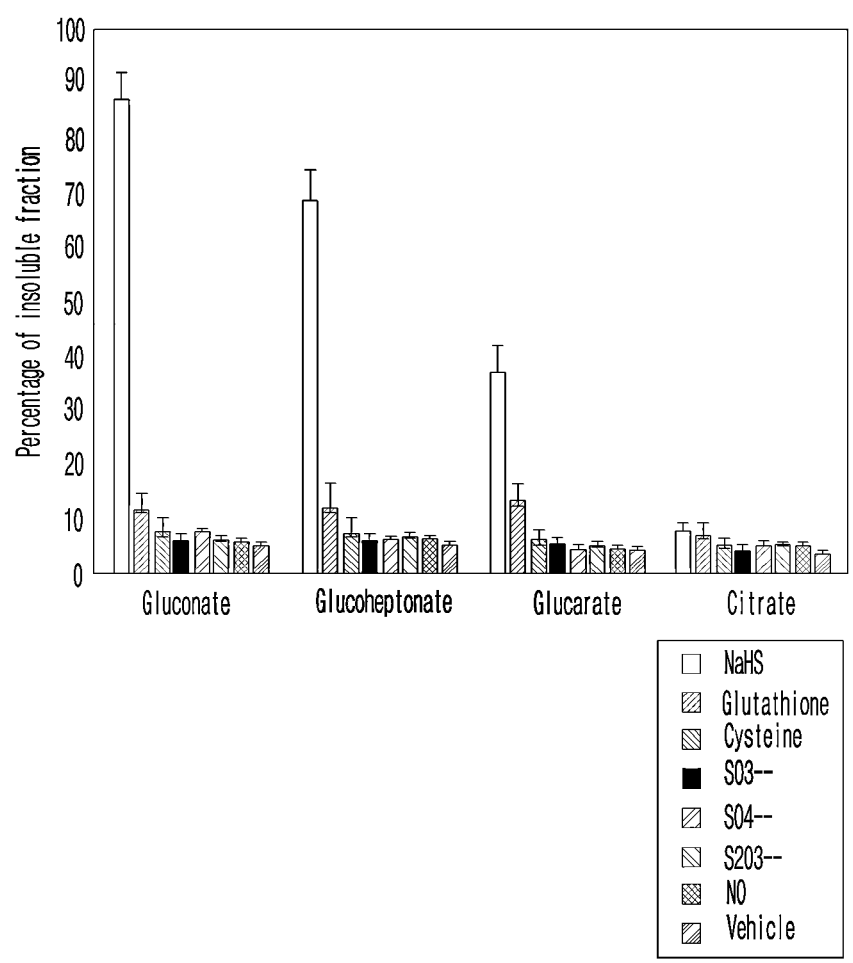
FIG. 8 is a graph showing the percentage of generating insoluble substances after the reaction of $^{99m}$Tc-alpha-hydroxy acid with NaHS and various active sulfides performed in Experimental Example 2.

Experimental Example 2: Evaluation of Reaction of $^{99m}$Tc-Alpha-Hydroxy Acid with NaHS and Various Active Sulfides In order to evaluate the reactivity of the $^{99m}$Tc-alpha-hydroxy acid according to the present invention with various active sulfides including NaHS (hydrogen sulfide), the following experiment was performed, and the results are shown in FIG. 8 and Table 1.

Particularly, the $^{99m}$Tc-alpha-hydroxy acid prepared in Example 1 was diluted 5 times with physiological saline, and then 100 μL of each diluent was taken, to which 100 μL of each of 0.2 M sodium phosphate buffer (pH 7.4) containing 0.4 mM NaHS, 4 mM glutathione, 0.4 mM cysteine, 0.4 mM sodium sulfite, 0.4 mM sodium sulfate, 0.4 mM sodium thiosulfate, and 0.4 mM NONOate (NO generating reagent) was added, followed by reaction at 37° C. for 15 minutes. Then, ITLC was developed with physiological saline to determine the percentage of the radioactivity remaining at the origin. When developed with physiological saline, the radioactivity remaining at the origin was made of an insoluble substance and was deposited on the site.

Table 1 below shows the percentage of insoluble substances produced after the reaction between $^{99m}$Tc-labeled alpha-hydroxy acid and active sulfides.

TABLE 1

|  | $^{99m}$Tc-gluconate | $^{99m}$Tc-glucoheptonate | $^{99m}$Tc-glucarate | $^{99m}$Tc-citrate |
| --- | --- | --- | --- | --- |
| NaHS | 87.8 ± 4.3 | 68.8 ± 5.7 | 37.0 ± 4.7 | 8.3 ± 1.0 |
| Glutathione | 12.0 ± 2.4 | 12.1 ± 4.5 | 13.4 ± 2.7 | 7.5 ± 1.7 |
| Cysteine | 5.1 ± 0.6 | 9.5 ± 0.8 | 6.4 ± 1.7 | 2.1 ± 0.2 |
| Sodium sulfite | 6.4 ± 0.7 | 10.7 ± 1.7 | 5.5 ± 0.8 | 7.8 ± 0.7 |
| Sodium sulfate | 7.9 ± 1.5 | 10.0 ± 1.3 | 4.6 ± 0.5 | 8.0 ± 0.5 |
| Thiosodium sulfate | 6.5 ± 1.0 | 8.9 ± 0.5 | 5.6 ± 0.3 | 5.5 ± 0.1 |
| NO | 6.1 ± 1.0 | 6.6 ± 0.9 | 4.7 ± 0.7 | 5.6 ± 0.4 |
| Buffer | 8.7 ± 1.8 | 10.4 ± 2.4 | 4.6 ± 0.5 | 4.0 ± 0.1 |

As shown in Table 1, $^{99m}$Tc-labeled gluconate, glucoheptonate, and glucarate reacted most with NaHS. Specifically, $^{99m}$Tc-gluconate produced 87.8±4.3% of insoluble substances, the most, $^{99m}$Tc-glucoheptonate produced 68.8±5.7% of insoluble substances, and $^{99m}$Tc-glucarate produced 37.0±4.7% of insoluble substances. On the other hand, $^{99m}$Tc-citrate produced 8.3±1.0% of insoluble substances, which was relatively low, but was the most reactive with hydrogen sulfide compared to other activated sulfides. Other $^{99m}$Tc-labeled alpha-hydroxy acids, $^{99m}$Tc-tartrate and $^{99m}$Tc-glucuronate prepared in Example 1 showed similar results to $^{99m}$Tc-citrate.

The results of Table 1 are summarized in a graph and shown in FIG. 8.

As shown in FIG. 8, $^{99m}$Tc-labeled gluconate, glucoheptonate, and glucarate reacted only with NaHS to produce 37.0~87.8% of insoluble substances but not with other active sulfides, which means that the reaction with active sulfides other than hydrogen sulfide was very low. On the other hand, $^{99m}$Tc-citrate did not produce much insoluble substances even by NaHS.

The $^{99m}$Tc-labeled alpha-hydroxy acid according to the present invention produced less than 15% of insoluble substances by reacting with active substances other than NaHS, such as glutathione, cysteine, sodium sulfite, sodium sulfate, thiosodium sulfate, NO and phosphate buffer. The $^{99m}$Tc-labeled alpha-hydroxy acid did not appear in the image due to the low production of insoluble substances.

That is, it was confirmed that the $^{9m}$Tc-labeled alpha-hydroxy acid according to the present invention selectively detects only NaHS (hydrogen sulfide) among active sulfides, and thus it can be effectively used for the detection of hydrogen sulfide.

Figure 9:
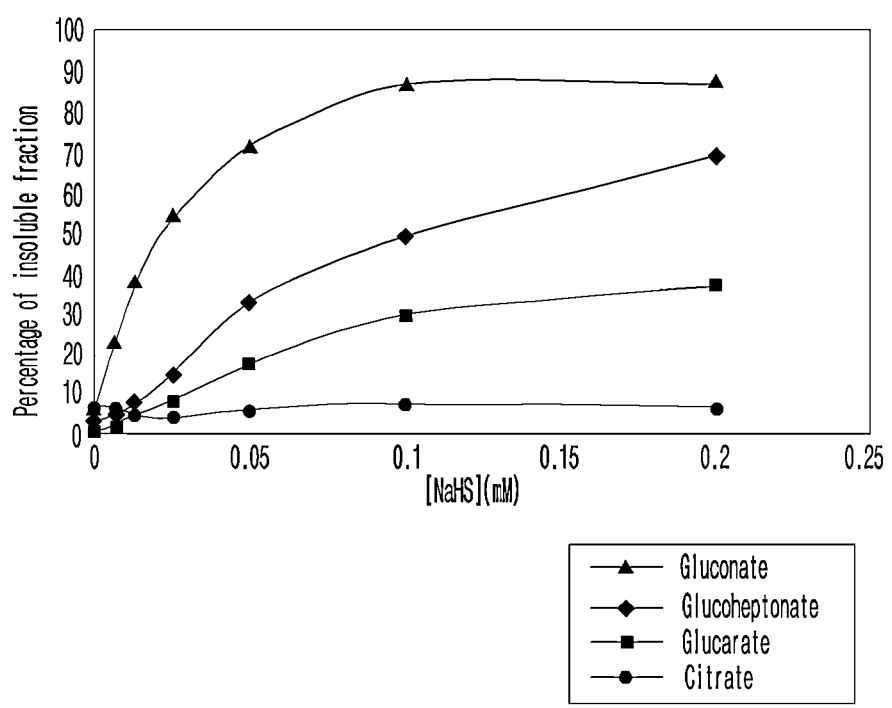
FIG. 9 is a graph showing the amount of insoluble substances produced by reacting $^{99m}$Tc-alpha-hydroxy acid with NaHS of different concentrations performed in Experimental Example 3.

Experimental Example 3: Evaluation of Reaction Degree of $^{99m}$Tc-Alpha-Hydroxy Acid According to NaHS Concentration In order to evaluate the reaction degree of the $^{99m}$Tc-alpha-hydroxy acid of the present invention according to the concentration of NaHS (hydrogen sulfide), the following experiment was performed, and the results are shown in FIG. 9.

Particularly, the $^{99m}$Tc-alpha-hydroxy acid prepared in Example 1 was diluted 5 times with physiological saline, and then 100 μL of each diluent was taken, to which 100 μL of 0.2 M sodium phosphate buffer (pH 7.4) containing 0~0.4 mM NaHS was added, followed by reaction at 37° C. for 15 minutes. Then, ITLC was developed with physiological saline to determine the percentage of insoluble substances.

As shown in Table 9, $^{99m}$Tc-gluconate reacted with hydrogen sulfide to produce the most insoluble substances, and it was confirmed that the production of insoluble substances increased as the concentration increased at the concentrations below 0.1 mM. However, equilibrium was reached at the concentrations above 0.1 mM.

It was confirmed that $^{99m}$Tc-glucoheptonate gradually increased the production of insoluble substances as the concentration of hydrogen sulfide increased.

It was also confirmed that $^{99m}$Tc-glucarate gradually increased the production of insoluble substances as the concentration of hydrogen sulfide increased.

On the other hand, it was confirmed that $^{99m}$Tc-citrate hardly produced insoluble substances.

From the above results, it was confirmed that the production of insoluble substances by the $^{99m}$Tc-alpha-hydroxy acid of the present invention varied depending on the concentration of hydrogen sulfide, and thus, it can be effectively used for measuring the concentration of hydrogen sulfide.

Experimental Example 4: Observation of Imaging of Inflamed Tissue where Hydrogen Sulfide Produced It has been reported that hydrogen sulfide was generated in the inflamed tissue induced by the administration of carrageenan (Li L, Bhatia M, Zhu Y Z, et al. FASEB J. (2005) 19:1196-1198; Bhatia M, Sidhapuriwala J, Moochhala S M, et al. Br J Pharmacol. (2005) 145:141-144.). Accordingly, the following experiment was performed to confirm whether the imaging of the inflamed tissue where hydrogen sulfide was generated was possible when the $^{99m}$Tc-alpha-hydroxy acid according to the present invention was administered.

<4-1> Imaging of Inflamed Tissue

30 μL of physiological saline containing 1% carrageenan was injected into the right hind paw of a mouse, and 30 μL of physiological saline was injected into the left hind paw of the mouse. After 4 hours, 300 μCi of $^{99m}$Tc-gluconate or $^{99m}$Tc-glucoheptonate labeled in Example 1 was injected into the tail vein of the mouse. After 1 hour, the hind paws were taken with SPECT-CT, and the results are shown in FIG. 10.

As shown in FIG. 10, both images showed the results of high radioisotope intake in the feet in which inflammation was induced.

In other words, both $^{99m}$Tc-gluconate and $^{99m}$Tc-glucoheptonate showed that the radioactivity of the inflamed area administered with carrageenan was clearly higher than that of the area administered with physiological saline. Therefore, it was proved that it is possible to image the inflamed area where hydrogen sulfide was produced.

<4-2> Evaluation of Hydrogen Sulfide Concentration in Inflamed Area

In order to confirm that the concentration of hydrogen sulfide in the inflamed area was higher than the concentration of hydrogen sulfide in the normal area, it was measured as follows using a method described in the literature (A D Ang, A Konigstorfer, G I Giles, M Bhatia. Adv Biol Chem, 2012, 2:360-365). After 4 hours, the mouse was euthanized with carbon dioxide gas, and the ankle was cut and the weight was measured. 500 μL of 50 mM sodium carbonate buffer (pH 9) chilled with ice was added thereto and homogenized for 30 seconds gently, 1 minute 30 seconds moderately, and 30 seconds vigorously. After centrifugation at 1200×g for 5 minutes, the supernatant was obtained, to which 400 μL of a mixed solution of 350 μL of 1% zinc acetate and 50 μL of 1.5 M sodium hydroxide was added, followed by mixing well. After centrifugation at 1200×g for 5 minutes, the supernatant was discarded. To the precipitated pellet, 1 mL of distilled water saturated with nitrogen was added, which was mixed by vortexing for 1 minute. After centrifugation at 1200×g for 5 minutes, the supernatant was discarded. 160 μL of 25 mM sodium hydroxide solution containing 1 g/L of ascorbic acid was added to the pellet and mixed well. 20 μL of 47.5 mM DMPD dissolved in 7.2 M hydrochloric acid and 20 μL of 80 mM $FeCl_3$ dissolved in 1.2 M hydrochloric acid were added thereto and vortexed for 10 seconds. After reacting at room temperature for 15 minutes, absorbance was measured at 665 nm. A standard quantification curve was drawn with a standard sample measured by the same method, and then quantified.

As a result of the quantification, the concentration of hydrogen sulfide in the paws treated with physiological saline was 19.8±4.4 μM (n=3), whereas the concentration of hydrogen sulfide in the paws treated with carrageenan was 43.7±3.5 μM (n=3), which was more than doubled. Therefore, it was confirmed that the increased intake of $^{99m}$Tc-gluconate and $^{99m}$Tc-glucoheptonate was correlated with the increase of hydrogen sulfide concentration.

The $^{99m}$Tc-alpha-hydroxy acid according to the present invention can image the inflamed tissue in which hydrogen sulfide is generated, and the concentration increase can be known through whether the intake of the treated $^{99m}$Tc-alpha-hydroxy acid increases, so that not only imaging but also the increase in concentration can be confirmed. In addition, since the hydrogen sulfide concentration can be quantified and expressed numerically through fluorescence assay, it can be effectively used to measure the concentration of hydrogen sulfide in the inflamed tissue.

Experimental Example 5: Observation of Imaging of Mouse Brain Reperfused after Middle Cerebral Artery Occlusion It has been reported that the concentration of hydrogen sulfide in the brain increased 12 hours after the blood flow in the mouse brain was blocked and reperfused (Ren C, Du A, Li D, et al. Brain Res. (2010) 1345:197-205.). Accordingly, the following experiment was performed to confirm whether the concentration of hydrogen sulfide can be measured and imaged in the reperfused mouse brain after middle cerebral artery occlusion when the $^{99m}$Tc-alpha-hydroxy acid according to the present invention was administered, and the results are shown in FIG. 11.

Particularly, a reperfusion model after middle cerebral artery occlusion was constructed according to the method of Koizumi et al. (Koizumi J, Yoshida Y, Nakazawa T, et al. Jpn J Stroke (1986) 8:1-8). The mouse was anesthetized by intramuscular injection of ketamine (80 mg/kg) and the carotid artery, the internal carotid artery, and the external carotid artery were separated in order by incising the skin of the neck. Then, a hole was made in the external carotid artery with a 27 gauge needle, and a nylon 4.0 thread coated with silicone was inserted about 17 mm to close the middle cerebral artery, and after 2 hours, the nylon thread was removed again to resume blood flow. The skin of the mouse was sutured and recovered for 12 hours, and then 1 mCi of the $^{99m}$Tc-gluconate prepared in Example 1 and 1 mCi of [$^{18}$F] FDG were mixed and administered to the tail vein of the mouse. After 1 hour, the mouse was anesthetized with ether and the brain was extracted by dissecting the skull. Coronal sections of 1 mm thick were made with the extracted brain, frozen, and exposed to a BAS2500 image plate (Fuji Film Co.) for 20 minutes in a −20° C. freezer. The sections were left for 20 hours to attenuate the radioactivity of $^{18}$F and exposed to the image plate for 24 hours in the freezer. The exposed tissues were stained in 1% 2,3,5-tetrazolium chloride (TTC) solution. In FIG. 11, TTC staining represents the living brain tissues, [$^{18}$F] FDG represents the degree of glucose metabolism, and $^{99m}$Tc-gluconate represents the generation site of hydrogen sulfide.

As shown in FIG. 11, the living tissues were stained red by TTC. [$^{18}$F] FDG image showed glucose metabolism, and it can be seen that it almost overlapped with the red area stained by TTC. $^{99m}$Tc-gluconate was ingested in the damaged area after reperfusion because it was ingested at the boundary area rather than completely dead brain tissues and the normal brain tissues, and it can be estimated that hydrogen sulfide generation was high in that area.

From the above results, it was confirmed that hydrogen sulfide was generated in the reperfused tissue, as the concentration of hydrogen sulfide increased in the reperfused tissue after middle cerebral artery occlusion.

In addition, it was confirmed that hydrogen sulfide detection, concentration measurement, and imaging of reperfused tissue after middle cerebral artery occlusion were possible using the $^{99m}$Tc-alpha-hydroxy acid according to the present invention.

Experimental Example 6: Confirmation of $^{99m}$Tc Accumulation in Tissue Administered with $^{99m}$Tc-Alpha-Hydroxy Acid The following experiment was performed to confirm whether the $^{99m}$Tc was accumulated when the $^{99m}$Tc-alpha-hydroxy acid according to the present invention was administered to the tissue containing hydrogen sulfide.

Particularly, NaHS was dissolved in matrigel at the concentration of 1.7 mg/mL and injected subcutaneously into the back of a BALB/c mouse by 50 μL, and 1 mCi of $^{99m}$Tc-gluconate was injected into the tail vein. One hour later, the matrigel was collected, weighed, and the radioactivity was measured. Using the results, the ingested amount (% ID/g) was calculated for the injected amount per tissue weight.

The composition for detecting hydrogen sulfide or measuring a concentration of hydrogen sulfide according to the present invention, which comprises the compound represented by formula 1 ($^{99m}$Tc-alpha-hydroxy acid) having alpha-hydroxy acid labeled with $^{99m}$Tc could selectively detect only hydrogen sulfide among various active sulfides, and the degree of generation of insoluble substances was changed according to the concentration of hydrogen sulfide.

Using the composition of the present invention, the concentration of hydrogen sulfide could be measured, imaging of the inflamed tissue in which hydrogen sulfide was generated, and the increase in the concentration of the generated hydrogen sulfide could be confirmed, and the hydrogen sulfide concentration could be quantified and expressed numerically through fluorescence assay. In addition, it was confirmed that hydrogen sulfide detection, concentration measurement, and imaging of reperfused tissue after middle cerebral artery occlusion were possible using the composition of the present invention.

Therefore, the composition for detecting hydrogen sulfide or measuring a concentration of hydrogen sulfide according to the present invention, which comprises the compound represented by formula 1 ($^{99m}$Tc-alpha-hydroxy acid) having alpha-hydroxy acid labeled with $^{99m}$Tc, enables the detection or concentration measurement of hydrogen sulfide in in-vitro and in-vivo levels and, as such, can be advantageously used for detecting hydrogen sulfide and measuring a concentration of hydrogen sulfide and furthermore for discovering biological roles of hydrogen sulfide in vivo, especially, for detecting, imaging, and quantitatively measuring hydrogen sulfide in a disease selected from the group consisting of angiogenesis, inflammation, cancer, Alzheimer's disease, cardiovascular ischemia, and cerebrovascular ischemia, or in hypoxic tissues.

In addition, $^{99m}$Tc is easier to supply than other radioactive isotopes and is competitive in price, so it has an economic advantage.

INDUSTRIAL APPLICABILITY

The composition for detecting hydrogen sulfide or measuring a concentration of hydrogen sulfide according to the present invention, which comprises the compound represented by formula 1 ($^{99m}$Tc-alpha-hydroxy acid) having alpha-hydroxy acid labeled with $^{99m}$Tc, enables the detection or concentration measurement of hydrogen sulfide in in-vitro and in-vivo levels and, as such, can be advantageously used for detecting hydrogen sulfide and measuring a concentration of hydrogen sulfide and furthermore for discovering biological roles of hydrogen sulfide in vivo, especially, for detecting, imaging, and quantitatively measuring hydrogen sulfide in a disease selected from the group consisting of angiogenesis, inflammation, cancer, Alzheimer's disease, cardiovascular ischemia, and cerebrovascular ischemia, or in hypoxic tissues.

What is claimed is:

1. A method for detecting endogenous hydrogen sulfide comprising a step of treating tissue or cells with a compound of an alpha-hydroxy acid labeled with $^{99m}$Tc in the presence of a phosphate buffer,
   and a step of imaging by reacting the compound with endogenous hydrogen sulfide in the presence of the phosphate buffer to form an insoluble material,
   wherein said alpha-hydroxy acid is D-gluconic acid, D-glucoheptonic acid or D-glucaric acid.

2. The method for detecting endogenous hydrogen sulfide according to claim 1, wherein the method comprises detecting endogenous hydrogen sulfide in the tissues or cells isolated from animal subjects.

3. The method for detecting endogenous hydrogen sulfide according to claim 1, wherein the method comprises detecting endogenous hydrogen sulfide in a disease selected from the group consisting of angiogenesis, inflammation, cancer, Alzheimer's dementia, cardiovascular ischemia, cerebrovascular ischemia and hypoxia.

4. The method for detecting endogenous hydrogen sulfide according to claim 1, wherein one or more adjuvants selected from reducing agents, stabilizers, excipients or buffers can be further used.

5. The method for detecting endogenous hydrogen sulfide according to claim 1, wherein the method comprises measuring a concentration of endogenous hydrogen sulfide.

6. The method for detecting endogenous hydrogen sulfide according to claim 1, where the method comprises imaging a disease in which endogenous hydrogen sulfide is generated.

7. The method for detecting endogenous hydrogen sulfide according to claim 6, wherein the disease is selected from the group consisting of angiogenesis, inflammation, cancer, Alzheimer's dementia, cardiovascular ischemia, cerebrovascular ischemia and hypoxia.

8. The method for detecting endogenous hydrogen sulfide according to claim 6, wherein the disease is selected from the group consisting of rheumatoid arthritis, non-rheumatic inflammatory arthritis, arthritis related to Lyme disease, pyelonephritis, nephritis, inflammatory osteoarthritis, meningitis, osteomyelitis, inflammatory bowel disease, appendicitis, pancreatitis, sepsis, inflammatory disease due to bacterial infection, myocardial infarction, heart ischemia, angina, angina pectoris, cardiomyopathy, endocarditis, arteriosclerosis, sepsis, diabetes, stroke, cirrhosis, asthma, Parkinson's disease, Alzheimer's disease, dementia, Down's syndrome, lung cancer, breast cancer, uterine cancer, ovarian cancer, liver cancer, brain cancer, prostate cancer, thyroid cancer, neuroendocrine tumor, stomach cancer, colon cancer, pancreatic cancer, bladder cancer, esophageal cancer and head/neck cancer.

9. The method for detecting endogenous hydrogen sulfide according to claim 1, wherein a disease in which endogenous hydrogen sulfide is generated is diagnosed by detecting endogenous hydrogen sulfide.

10. The method for detecting endogenous hydrogen sulfide according to claim 9, wherein the disease is selected from the group consisting of angiogenesis, inflammation, cancer, Alzheimer's dementia, cardiovascular ischemia, cerebrovascular ischemia and hypoxia.

11. The method for detecting endogenous hydrogen sulfide according to claim 9, wherein the disease is selected from the group consisting of rheumatoid arthritis, non-rheumatic inflammatory arthritis, arthritis related to Lyme disease, pyelonephritis, nephritis, inflammatory osteoarthritis, meningitis, osteomyelitis, inflammatory bowel disease, appendicitis, pancreatitis, sepsis, inflammatory disease due to bacterial infection, myocardial infarction, heart ischemia, angina, angina pectoris, cardiomyopathy, endocarditis, arteriosclerosis, sepsis, diabetes, stroke, cirrhosis, asthma, Parkinson's disease, Alzheimer's disease, dementia, Down's syndrome, lung cancer, breast cancer, uterine cancer, ovarian cancer, liver cancer, brain cancer, prostate cancer, thyroid cancer, neuroendocrine tumor, stomach cancer, colon cancer, pancreatic cancer, bladder cancer, esophageal cancer and head/neck cancer.

12. The method for detecting endogenous hydrogen sulfide according to claim 4, wherein the adjuvant is at least one selected from $SnCl_2$, ascorbic acid, gentisinic acid, calcium chloride, sodium chloride, sodium phosphate, mannitol, glucose, lactose or sodium ascorbate.

13. A method for detecting endogenous hydrogen sulfide comprising a step of administering a compound of an alpha-hydroxy acid labeled with $^{99m}Tc$ to a subject intravenously, and a step of imaging by reacting the compound with endogenous hydrogen sulfide to form an insoluble material, wherein said alpha-hydroxy acid is D-gluconic acid, D-glucoheptonic acid or D-glucaric acid.

14. The method of claim 1, wherein reacting the compound with the hydrogen sulfide is performed at a pH of 7.4.

* * * * *